US00PP32761P2

(12) United States Plant Patent
Pineau

(10) Patent No.: US PP32,761 P2
(45) Date of Patent: Jan. 19, 2021

(54) ***HIBISCUS* PLANT NAMED 'MINSYWHI07'**

(50) Latin Name: ***Hibiscus* hybrid**
Varietal Denomination: MINSYWHI07

(71) Applicant: Hortival Diffusion SAS, Beaufort en Vallee (FR)

(72) Inventor: Patrick Pineau, Saint Mathurin sur Loire (FR)

(73) Assignee: Hortival Diffusion SAS

( * ) Notice: Subject to any disclaimer, the term of this patent is extended or adjusted under 35 U.S.C. 154(b) by 0 days.

(21) Appl. No.: 16/602,746

(22) Filed: Dec. 3, 2019

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
CPC ... A01H 5/02; A01H 5/00; A01H 6/60; A01H 6/608
See application file for complete search history.

(56) References Cited

U.S. PATENT DOCUMENTS

PP19,547 P2 * 12/2008 Shim ..... A01H 5/02 Plt./257
PP27,285 P2 * 10/2016 van Huylenbroeck .. A01H 5/02 Plt./257

* cited by examiner

*Primary Examiner* — June Hwu
(74) *Attorney, Agent, or Firm* — Cassandra Bright

(57) ABSTRACT

A new and distinct cultivar of *Hibiscus* plant named 'MINSYWHI07' is disclosed, characterized by large flowers colored white with a large red eye and long, well-defined lighter colored red-purple stripes, and dark green foliage. Plants are well branched and compact. The new variety is a *Hibiscus*, normally produced as an outdoor garden or container plant.

2 Drawing Sheets

Figure 1:
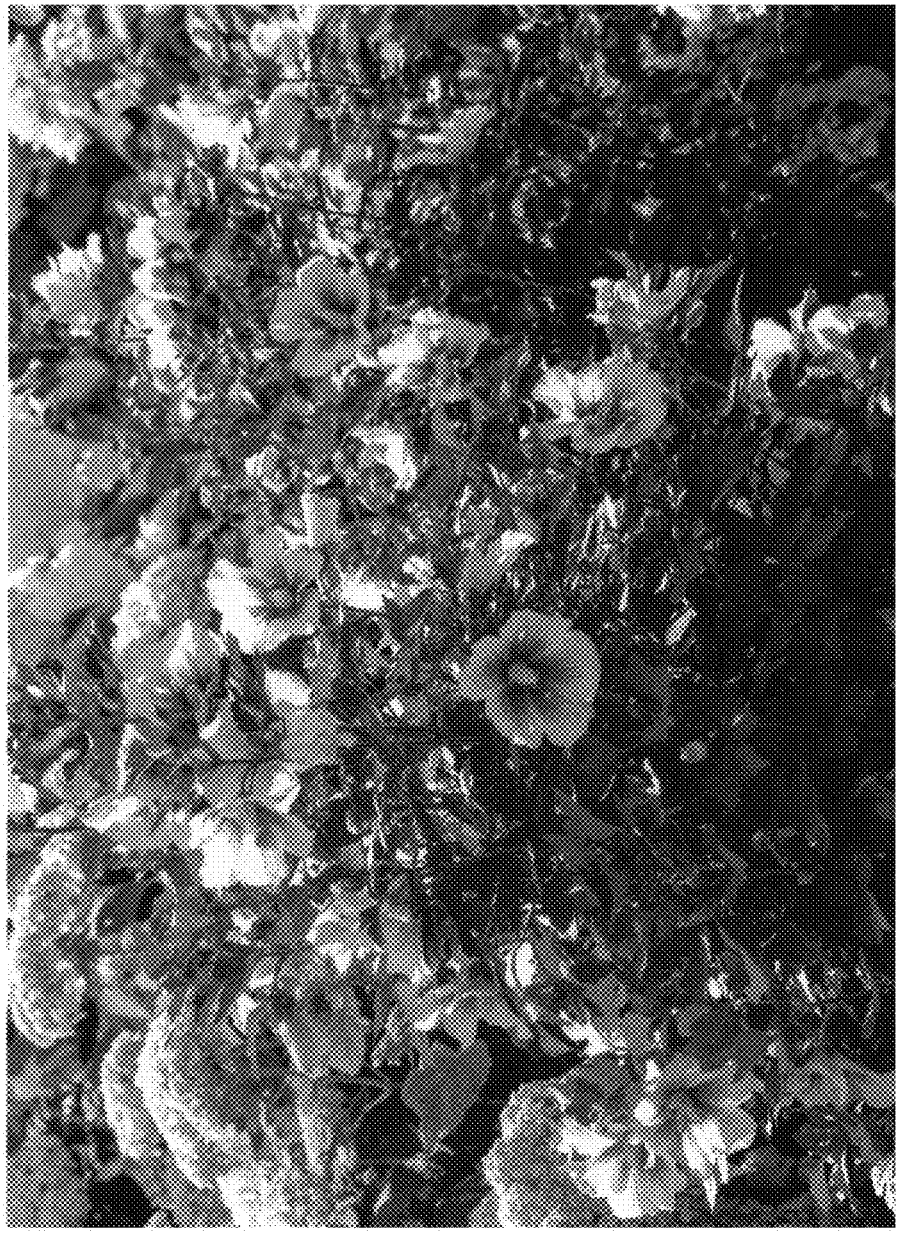

Latin name of the genus and species: *Hibiscus* hybrid.
Variety denomination: 'MINSYWHI07'.

BACKGROUND OF THE INVENTION

The new *Hibiscus* cultivar is a product of a planned breeding program conducted by the inventor, Patrick Pineau. The objective of the breeding program was to produce big flowers with large eyes. The cross resulting in this new variety was made in July 2008.

The seed parent is an unnamed, unpatented *Hibiscus* seedling from advanced internal selection '#11154'. The pollen parent is the unpatented variety *Hibiscus syriacus* 'Minrosa' (U.S. Plant patent application Ser. No. 09/642,987, abandoned). The new variety was identified and selected as a potentially interesting selection in September 2012. Selection was made at a nursery in La Menitre, Me. Et Loire, France. Date of first sale was Jun. 25, 2019, occurring in the United States. This sale was made directly by the inventor or one who obtained the claimed invention directly or indirectly from the inventor. This sale and all public disclosures made between Jun. 25, 2019 and the filing of this application fall within the exception allowed under 102(b)(1).

Asexual reproduction of the new cultivar 'MINSYWHI07' was first performed in February 2013 in La Menitre, Me. Et Loire, France, by wedge grafting. Subsequent propagation has shown that the unique features of this cultivar are stable and reproduced true to type in 6 successive generations.

SUMMARY OF THE INVENTION

The cultivar 'MINSYWHI07' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MINSYWHI07' These characteristics in combination distinguish 'MINSYWHI07' as a new and distinct *Hibiscus* cultivar:

1. Well branched and compact.
2. White flower with a large red eye and well-defined long, lighter red-purple stripes.
3. Large flowers.
4. Dark green foliage.

PARENT COMPARISON

Plants of the new cultivar 'MINSYWHI07' are similar to plants of the seed parent variety in most horticultural characteristics, however, plants of the new cultivar 'MINSYWHI07' differ in the following;

1. The new variety has white flowers with large red colored eyes and well-defined, long red stripes. The seed parent has white flowers with bi-colored centers (white and red) with finer long lighter red stripes.
2. The new variety has pink flower buds, while the seed parent has white flower buds.

Plants of the new cultivar 'MINSYWHI07' are similar to plants of the pollen parent variety in most horticultural characteristics, however, plants of the new cultivar 'MINSYWHI07' differ in the following;

1. The new variety has white flowers with large red colored eyes and well-defined, long, lighter red-purple stripes. The pollen parent has pink flowers with red colored centers.
2. The new variety has petals which are undulate, but less undulate than the pollen parent.
3. The new variety has darker and larger foliage than the pollen parent.

COMMERCIAL COMPARISON

Plants of the new cultivar 'MINSYWHI07' can be compared to the variety *Hibiscus syriacus* 'Antong Two', U.S. Plant Pat. No. 19,547. These varieties are similar in most horticultural characteristics however, 'MINSYWHI07' differs in the following:

1. Flowers of the new variety have-large, red colored eyes with long, well defined lighter colored red-purple stripes, while this comparator's flowers have distinctively shaped red eyes, with the blotch extending within the center of the individual petals, forming a kind of star-shaped eye. Eye coloration of the new variety is a single central blotch, which then extends as distinctive stripes.
2. Flowers of the new variety have smaller eyes than flowers of this comparator.
3. The new variety has darker green foliage than this comparator.

BRIEF DESCRIPTION OF THE PHOTOGRAPHS

The accompanying photograph in FIG. 1 illustrates in full color a typical plant of 'MINSYWHI07' grown in a #3 pot, in Grand Haven, Mich.

Figure 2:
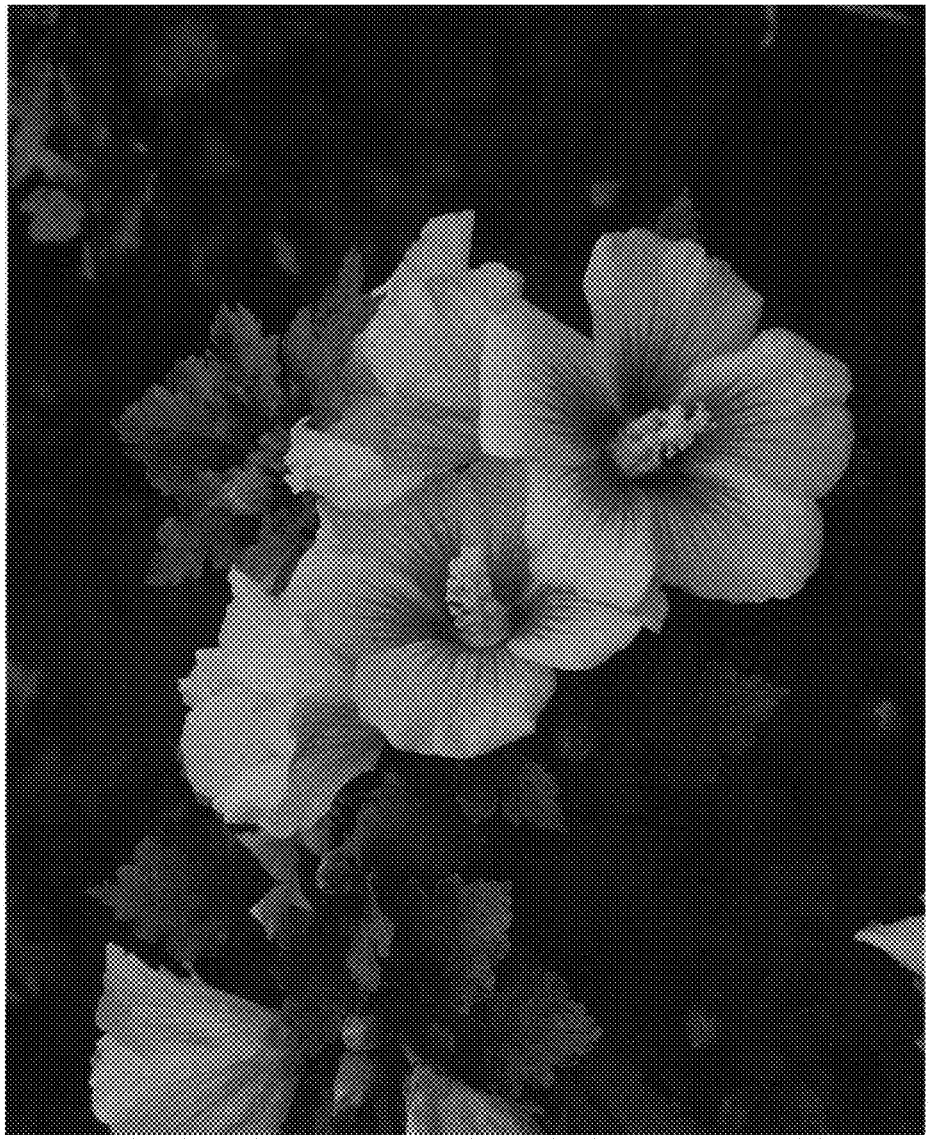

FIG. 2 illustrates in full color a typical flower of 'MINSYWHI07'.

Age of the plant photographed is approximately 3 years. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, 6$^{th}$ edition, except where general terms of ordinary dictionary significance are used. The following observations and measurements describe 'MINSYWHI07' plants grown in a polygreenhouse in Grand Haven, Mich., under natural lighting. Measurements were taken in August 2017. The plants were 2 years old in #3 containers. The growing temperature ranged from approximately −5° C. to 27° C. Measurements and numerical values represent averages of typical plant types.

Botanical classification: *Hibiscus* hybrid 'MINSYWHI07'.

PROPAGATION

Time to initiate roots: 20 days at approximately 25° C.

Root description: Fibrous, medium root thickness. Tan/brown in color, not effectively measured with a color chart.

Time to produce a rooted young plant: About 90 days at 25° C.

PLANT

Plant type: Perennial shrub.
Age of plant described: Approximately 2 years old.
Growth habit: Upright.
Height: 63 cm.
Spread: 56 cm.
Growth rate: Good.
Plant vigor: Good.
Branching characteristics: Basal.
Length of primary lateral branches: 46 cm.
Quantity of lateral branches: 10.
Characteristics of primary lateral branches:
- *Diameter.*—8 mm.
- *Color.*—New: RHS Green 138A. Woody: RHS Brown 200A.
- *Pubescence.*—On new growth.

Internode length: 4-6 cm.

FOLIAGE

Leaf:
- *Arrangement.*—Alternate, single.
- *Quantity.*—Approximately 25 per branch.
- *Average length.*—5.5 cm.
- *Average width.*—4.75 cm.
- *Shape of blade.*—Oblanceolate with 3 shallow lobes.
- *Apex.*—Acute.
- *Base.*—Oblique.
- *Margin.*—Lobed with moderate incisions.
- *Texture of top surface.*—Slightly rough, ribbed.
- *Texture of bottom surface.*—Rough, distinct veins.
- *Pubescence.*—None.
- *Color.*—Young foliage upper side: RHS Green 137A. Young foliage under side: RHS Green 143C. Mature foliage upper side: RHS Green 137A. Mature foliage under side: RHS Green 143C.
- *Venation.*—Type: Palmate. Venation color upper side: RHS Green 137C. Venation color under side: RHS Green 145A.
- *Petiole.*—Length: 3 cm. Diameter: 2 mm. Pubescence: Pubescent, both sides. Color: RHS Green 143A, both sides.

FLOWER

Natural flowering season: Summer.
Flower arrangement: Axillary, single rotate.
Flower type: Rotate.
Flowering habit: Whorl.
Quantity of flowers per lateral stem: 6.
Quantity of buds per lateral stem: 6.
Quantity of flowers and buds per plant: About 50.
Persistent or self-cleaning: Self-cleaning.
Bud:
- *Shape.*—Oval.
- *Length.*—2.75 cm.
- *Diameter.*—1.5 cm.
- *Color.*—RHS Green 143B.

Flower:
- *Diameter.*—11 cm.
- *Depth.*—5 cm.

*Aspect.*—Outward.
*Shape.*—Rotate.

Petals:
*Quantity.*—5.
*Appearance.*—Delicate with slightly undulate edges.
*Arrangement.*—Whorled, slightly overlapping.
*Length.*—6.5 cm.
*Width.*—6 cm.
*Shape.*—Obovate.
*Apex.*—Obtuse.
*Base.*—Attenuate.
*Margin.*—Undulate with weak or no incision.
*Texture, upper and lower surfaces.*—Smooth, soft.
*Color.*—When opening, upper surface: RHS Red-Purple 69D with striations of Red-Purple 71B. When opening, lower surface: RHS Red-Purple 69D with striations of Red-Purple 71B. Fully opened, upper surface: RHS White N155B with an eye of Red 53B and striations of Red-Purple 61B and 61C lighter color towards apex. Fully opened, lower surface: RHS White N155B with streaks of Red-Purple 61C.

Petaloids: None.

Sepals:
*Arrangement.*—Radial.
*Quantity.*—5.
*Length.*—1.2 cm.
*Width.*—2 mm.
*Shape.*—Narrowly triangular.
*Margin.*—Entire.
*Apex.*—Narrowly acute.
*Base.*—Truncate.
*Color, mature, both sides.*—RHS Green 143A.
*Texture.*—Rough, both sides.

Calyx:
*Shape.*—Funnelform.
*Length.*—2.25 cm.
*Diameter.*—1.5 cm.

Epicalyx:
*Quantity.*—5.
*Length.*—4 mm.
*Width.*—2 mm.
*Color, mature, both sides.*—RHS Green 143A.

Peduncles:
*Length.*—1.5 cm.
*Diameter.*—4 mm.
*Angle.*—15-45°.
*Strength.*—Good.
*Texture.*—Pubescent.
*Color.*—RHS Green 143B.

Pedicels: None.

Fragrance: None.

REPRODUCTIVE ORGANS

Stamens:
*Number.*—50.
*Filament length.*—2 mm.
*Filament color.*—RHS Green-White 157D.
*Staminal column length.*—Average 4 cm.

Anthers:
*Shape.*—Fused.
*Length.*—2 mm.
*Color.*—RHS White 155A.
*Pollen color.*—RHS White 155A.
*Pollen amount.*—Some.

Pistil:
*Number.*—1.
*Length.*—4.25 cm.
*Style.*—Length: 3.7 cm. Color: RHS White 155C.
*Stigma.*—Shape: Peltate. Color: RHS White 155A.
*Ovary color.*—RHS White 155C with light shading of Red-Purple 60B.

OTHER CHARACTERISTICS

Seeds and fruits: None observed.

Disease/pest resistance: Neither resistance nor susceptibility to normal diseases and pests of *Hibiscus* have been observed.

Garden performance: Good tolerance, performs well in humid conditions.

Temperature tolerance: Low temperature tolerance to at least USDA zone 4, high temperature tolerance to at least 40° C.

What is claimed is:

1. A new and distinct cultivar of *Hibiscus* plant named 'MINSYWHI07' as herein illustrated and described.

* * * * *